(12) United States Patent
Cha et al.

(10) Patent No.: US 9,005,992 B2
(45) Date of Patent: Apr. 14, 2015

(54) IMMOBILIZING FUSION PROTEIN FOR EFFECTIVE AND ORIENTED IMMOBILIZATION OF ANTIBODY ON SURFACES

(75) Inventors: Hyung Joon Cha, Pohang-si (KR); Chang Sup Kim, Pohang-si (KR)

(73) Assignee: Postech Academy-Industry Foundation, Pohang (KR)

( * ) Notice: Subject to any disclaimer, the term of this patent is extended or adjusted under 35 U.S.C. 154(b) by 1062 days.

(21) Appl. No.: 13/051,219

(22) Filed: Mar. 18, 2011

(65) Prior Publication Data

US 2012/0238039 A1 Sep. 20, 2012

(51) Int. Cl.
| | |
|---|---|
| G01N 33/543 | (2006.01) |
| G01N 33/531 | (2006.01) |
| G01N 21/65 | (2006.01) |
| C07K 14/435 | (2006.01) |

(52) U.S. Cl.
CPC ........ *G01N 33/54353* (2013.01); *G01N 33/531* (2013.01); *G01N 21/658* (2013.01); *C07K 14/43504* (2013.01); *C07K 2319/705* (2013.01); *C07K 2319/21* (2013.01)

(58) Field of Classification Search
None
See application file for complete search history.

(56) References Cited

U.S. PATENT DOCUMENTS

| | | | | |
|---|---|---|---|---|
| 5,817,470 | A * | 10/1998 | Burzio et al. | 435/7.9 |
| 8,673,986 | B2 * | 3/2014 | Cha et al. | 514/772.1 |
| 8,765,682 | B2 * | 7/2014 | Cha et al. | 514/19.1 |
| 2007/0042427 | A1 * | 2/2007 | Gerdes et al. | 435/7.1 |
| 2010/0261286 | A1 * | 10/2010 | Kim et al. | 436/149 |
| 2010/0266455 | A1 * | 10/2010 | Sommer | 422/100 |
| 2012/0202748 | A1 * | 8/2012 | Cha et al. | 514/19.1 |
| 2013/0052712 | A1 * | 2/2013 | Cha et al. | 435/177 |

FOREIGN PATENT DOCUMENTS

KR 10-2011-0051778 5/2011

OTHER PUBLICATIONS

Lin et al. "Adhesion mechanisms of the mussel foot proteins mfp-1 and mfp-3", vol. 104 No. 10 (2007).*
C. S. Kim, W. Ko, and H. J. Cha, "Novel linker material based on mussel adhesive protein fused with BC domain of protein A for efficient surface immobilization of antibody", Proceedings of the 239th ACS National Meeting, San Francisco, Mar. 21-25, 2010.
Chang Sup Kim, Wooree Ko and Hyung Joon Cha, "Effective Immobilization of Antibodies with Fc-specific BC Domains-fused Mussel Adhesive Protein", Proceedings of the 2010 KSBB Spring Meeting and International Symposium, Kyungwon University, Korea, Apr. 15-16, 2010.
Chang Sup Kim, Wooree Ko and Hyung Joon Cha, "A novel material of BC-mussel adhesive protein fusion protein for efficient immobilization of antibody", Proceeding of the 2010 KIChE Spring Meeting, Theories and Applications of Chemical Engineering, vol. 16, No. 1, 2010, p. 402.

* cited by examiner

*Primary Examiner* — Anh Lam
(74) *Attorney, Agent, or Firm* — Lexyoume IP Meister, PLLC

(57) ABSTRACT

The present invention relates to a novel fusion protein comprising Staphylococcal protein A and mussel adhesive protein, a biochip comprising a solid substrate to which the fusion protein is attached, and a method for detecting a target antigen in a biological sample using the biochip. Furthermore, the present invention relates to a polynucleotide encoding the fusion protein, a recombinant vector comprising the polynucleotide, a transformed cell comprising the recombinant vector, and a method of preparing the fusion protein by transformed cell comprising the recombinant vector.

19 Claims, 8 Drawing Sheets

IMMOBILIZING FUSION PROTEIN FOR EFFECTIVE AND ORIENTED IMMOBILIZATION OF ANTIBODY ON SURFACES

BACKGROUND OF THE INVENTION (a) Field of the Invention

The present invention relates to a novel fusion protein comprising Staphylococcal protein A and mussel adhesive protein, a biochip comprising a solid substrate to which the fusion protein is attached, and a method for detecting a target antigen in a biological sample using the biochip. Furthermore, the present invention relates to a polynucleotide encoding the fusion protein, a recombinant vector comprising the polynucleotide, a transformed cell comprising the recombinant vector, and a method of preparing the fusion protein by transformed cell comprising the recombinant vector.

(b) Description of the Related Art

Early detection of diseases is a key for their successful treatments despite of advancement of therapeutic tools. Immunoassay is one of the vital technologies for disease diagnosis due to high specificity and affinity of antibodies to target antigens. In most of immunoassays, antibody-antigen interactions are measured on solid supports. Because effective immobilization of antibody on solid support controls specificity and sensitivity of assay devices, immobilization of antibody with efficient manner is crucial and one of key issues for various fields including immunoassays and immunosensors.

Antibodies have been immobilized on solid supports by diverse methods including physical adsorption and covalent binding (R. Pei, X. Yang, E. Wang, *Analyst* 2001, 126, 4.; A. Subramanina, J. Irudayaraj, T. Ryan, *Biosens. Bioelectron.* 2006, 21, 998.). However, these methods have been suffered from reduced antibody activity (that is, antigen binding ability) due to random orientation, denaturation, and chemical modification of antibodies (G. T. Hermanson, *Bioconjugate Techniques*, Academic press, California 1996.; H. Zhu, M. Synder, *Curr. Opin. Chem. Biol.* 2003, 7, 55.). Therefore, antibody-binding proteins such as protein A and G have been widely employed to overcome limitations of the previous physical and chemical methods. Those proteins specifically recognize and bind to Fc region of antibodies with high affinity, and realized oriented-immobilization of antibodies on surfaces without reduced antibody activity (M. D. P. Boyle, K. J. Reis, *Biotechnology* 1987, 5, 697.; W. L. Hoffman, D. J. O' Shannessy, *J. Immunol. Methods* 1998, 112, 113.). Thus, the antibody-binding protein-based antibody immobilization methods have significantly improved antigen-binding ability, sensitivity, and stability compared to the previous methods.

However, efficient attachment of antibody-binding proteins on solid surfaces still remains as a major challenge. For efficient binding with functional orientation, antibody-binding proteins have been fused with several biomolecules such as cysteine residue(s), oligonucleotide, hexahistidine ($His_6$) peptide, gold-binding peptide, and glutathione-S-transferase (J. M. Lee, et al., *Anal. Chem.* 2007, 79, 2680.; Y. Jung, et al., *Anal. Chem.* 2007, 79, 6534.; S. M. Patrie, et al., *Anal. Chem.* 2007, 79, 5878.; S. Ko, et al., *Biosens. Bioelectron.* 2009, 24, 2592.; T. H. Ha, et al., *Anal. Chem.* 2007, 79, 546.). However, the above fusion proteins have still limitation because immobilization is possible onto only corresponding reactive group-derived surfaces. For protein immobilization, preparation of modified surface is time-consuming and sometimes difficult for non-experts.

Mussel adhesive proteins (MAPs) from marine mussels are water-insoluble bioadhesives that adhere tightly to substrata. MAPs are able to form strong bond to diverse substrates including glass, metal, and plastics without any surface pre-treatments (J. H. Waite, *Int. J. Adhesion Adhesive* 1987, 7, 9.; L. O. Burzio, et al., *The Japanese Soc. Mar. Biotechnology.*, Tokyo, 1989.). However, the amounts of MAPs that can be extracted directly from mussels are extremely low and attempts to produce functional recombinant MAPs have been failed (D. Morgan, *Scientist* 1990, 4, 1; M. Kitamura, et al., *J. Polym. Sci. Ser. A* 1999, 37, 729; A. J. Salerno, et al., *Appl. Microbiol. Biotechnol.* 1993, 58, 209.).

In the present work, we constructed a novel molecule, BC-MAP, as a functional immobilizing linker by genetic fusion of MAP with two domains (B and C) of protein A for facile and effective immobilization of antibodies on diverse solid supports with oriented manner without any additional steps and/or pretreatments. A representative scheme of effective immobilization of antibody onto diverse surfaces using functional BC-MAP linker material is shown in FIG. 8.

SUMMARY OF THE INVENTION

The present invention provides a fusion protein comprising protein A or a peptide derived from protein A and mussel adhesive protein or a peptide derived from a mussel adhesive protein.

The present invention also provides a polynucleotide encoding the fusion protein.

The present invention also provides a recombinant vector comprising the polynucleotide.

The present invention also provides a transformed cell comprising the recombinant vector.

The present invention also provides a method of preparing the fusion protein by transformed cell comprising the recombinant vector.

The present invention also provides a biochip comprising a solid substrate to which the fusion protein is attached.

The present invention also provides a method for detecting a target antigen in a biological sample using the biochip.

BRIEF DESCRIPTION OF THE DRAWINGS

FIG. 7(a) shows QCM response for the binding of BC and BC-MAP on gold at flow rate 50 μL min$^{-1}$.

FIG. 7(b) shows QCM response for the binding of antibody on BC- and BC-MAP-coated gold at a flow rate of 50 μL min$^{-1}$ and.

FIG. 7(c) shows data analysis of frequency shift upon the binding of BC and BC-MAP on gold at a flow rate of 50 μL min$^{-1}$. Values are the means from three independent experiments. Standard derivations are indicated in bar graphs.

FIG. 7(d) shows data analysis of frequency shift upon the binding of antibody on BC- and BC-MAP-coated gold at a flow rate of 50 μL min$^{-1}$. Values are the means from three independent experiments. Standard derivations are indicated in bar graphs.

DETAILED DESCRIPTION OF THE EMBODIMENTS

Figure 1:
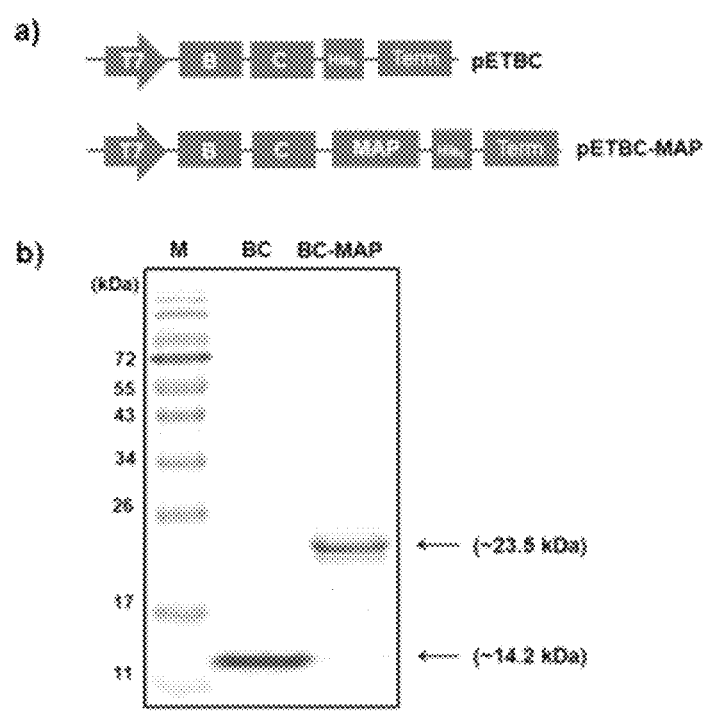
FIG. 1(a) shows schematic representation of pET-BC-MAP and pET-BC plasmids for the expression of BC-MAP fusion protein and BC domain protein used in the present invention.
FIG. 1(b) shows Coomassie-blue-stained SDS-PAGE analysis of purified BC-MAP and BC. Lane: M, molecular weight.

In the following detailed description, only certain exemplary embodiments of the present invention have been shown and described, simply by way of illustration.

As those skilled in the art would realize, the described embodiments may be modified in various ways, all without departing from the spirit or scope of the present invention.

Accordingly, the drawings and description are to be regarded as illustrative in nature and not restrictive.

Like reference numerals designate like elements throughout the specification.

In addition, unless explicitly described to the contrary, the word "comprise", and variations such as "comprises" or "comprising", will be understood to imply the inclusion of stated elements, but not the exclusion of any other elements.

In one aspect, the present invention relates to a fusion protein comprising protein A or a peptide derived from protein A and a mussel adhesive protein or a peptide derived from a mussel adhesive protein.

In a strategy to immobilize antibodies efficiently on surfaces in order to assess sensitivity and specificity of various immunosensors and immunoassays, the present invention intends to provide a fusion protein in which a mussel adhesive protein is fused to a antibody-binding protein, especially protein A derived from *Staphylococcus Aureus* or a peptide derived from protein A.

The proposed fusion protein of the present invention could be an invaluable linker material to facilitate an efficient immobilization of antibodies onto diverse solid supports.

The term "antibody-binding protein" as used herein refers to a protein that specifically recognizes and binds to Fc region of antibodies with high affinity, and realizes oriented-immobilization of antibodies on surfaces without reduced antibody activity. Preferably, the antibody-binding protein includes a protein A derived from *Staphylococcus aureus* or a peptide derived from protein A.

In one embodiment, the protein A has an amino acid sequence of SEQ ID No: 7.

In another embodiment, the peptide derived from protein A comprises a peptide or polypeptide comprising continuous subsequence of protein A that is capable of binding to Fc region of antibodies.

Preferably, the peptide derived from protein A comprises an amino acid sequence of 50 to 500 continuous amino acid residues, more preferably, 58 to 500 continuous amino acid residues of amino acid sequence of SEQ ID No:7. In a preferred embodiment, the peptide derived from protein A is a protein, a fragment, and a fusion peptide of at least one selected from the group consisting of domain A, domain B, domain C, domain D, domain E, or BC domain of the protein A.

In another embodiment, the peptide derived from of protein A is a protein, a fragment, and a fusion peptide of at least one selected from group consisting of domain A having an amino acid sequence of SEQ ID No: 8, domain B having an amino acid sequence of SEQ ID No:9, domain C having an amino acid sequence of SEQ ID No: 10, domain D having an amino acid sequence of SEQ ID No: 11 and domain E having an amino acid sequence of SEQ ID No: 12.

In another embodiment, the peptide derived from protein A is BC domain of the protein A having an amino acid sequence of SEQ ID No: 13.

The term "mussel adhesive protein (MAP)" as used herein refers to a protein from marine mussels and is water-insoluble bioadhesives that adhere tightly to substrata. MAP is able to form a strong bond to diverse substrates including glass, metal, and plastics without any surface pretreatment. In the present invention, MAP acts as an immobilization agent for antibodies.

The peptide derived from the mussel adhesive protein in the present invention comprises a protein, a fragment, and a fusion peptide of at least one selected from mussel foot protein (FP)-1, FP-2, FP-3, FP-4, FP-5, and FP-6.

In one embodiment, the FP-5 comprises an amino acid sequence of SEQ ID No: 6.

The term "fusion protein" as used herein, generally indicates a polypeptide in which heterogenous polypeptides having different origins are linked, and in the present invention, refers to a polypeptide in which an antibody-binding protein and a MAP are linked.

In one embodiment, the protein A or a peptide derived from protein A is fused to the N-terminus or C-terminus of MAP or a peptide derived from MAP.

In another embodiment, the fusion protein comprises MAP having an amino acid sequence of SEQ ID No: 6, and protein A is fused to the N-terminus or C-terminus of MAP. Preferably, the fusion protein comprises BC domain of the protein A fused to the N-terminus or C-terminus of MAP having an amino acid sequence of SEQ ID No: 6. More preferably, the fusion protein comprises BC domain of the protein A having an amino acid sequence of SEQ ID No: 13 fused to the N-terminus or C-terminus of MAP having an amino acid sequence of SEQ ID No: 6, which in turn forms a fusion protein having an amino acid sequence of SEQ ID No: 14.

This fusion protein may be obtained by chemical synthesis, or expression and purification processes of genetic recombination. Preferably, a hybrid gene, in which a gene sequence encoding an antibody-binding protein is linked to another gene sequence encoding a MAP, is expressed in a cell expression system. Then, the present fusion protein may be produced by transforming a host cell with a recombinant vector, and isolating and purifying a fusion protein expressed by the host cell.

In such a fusion protein, the antibody-binding protein and the MAP may be linked directly or by means of a connector, such as a linker. When a linker is used, it should not negatively affect the induction of antibody immobilization by the fusion protein.

Thus, in another aspect, the present invention relates to a polynucleotide encoding the fusion protein, a recombinant vector comprising the polynucleotide, and a transformed cell comprising the recombinant vector.

In a further aspect, the present invention relates to a method of preparing the fusion protein by transformed cell comprising the recombinant vector.

A process of producing the fusion protein of the present invention by genetic recombination comprises the following four steps.

The first step is to insert a gene encoding the fusion protein into a vector to construct a recombinant vector. Preferably, a gene encoding the fusion protein has a nucleotide acid sequence of SEQ ID No: 15, but not limited thereto.

A vector into which a gene encoding the fusion protein is introduced may be a plasmid, a virus, a cosmid, or the like. The recombinant vector includes a cloning vector and an expression vector. A cloning vector contains a replication origin, for example, a replication origin of a plasmid, pharge or cosmid. The origin may be characterized as a "replicon" at which the replication of an exogenous DNA fragment attached thereto is initiated. An expression vector is developed for use in protein synthesis. A recombinant vector serves as a carrier for a foreign DNA fragment inserted thereto, which typically means a double-stranded DNA fragment. The term "foreign DNA" as used herein refers to DNA derived from a heterogeneous species, or a substantially modified form of native DNA from a homogenous species. In this case, a foreign gene is a specific target nucleic acid to be transcribed to encode a polypeptide.

The recombinant vector contains a target gene that is operably linked to transcription and translation expression regulatory sequences, which exert their functions to a selected host cell, in order to increase expression levels of the transfected gene in the host cell. The recombinant vector is a genetic construct that contains essential regulatory elements to which a gene insert is operably linked to be expressed in cells of an individual. Such a genetic construct is prepared using a standard recombinant DNA technique. The type of the recombinant vector is not specifically limited as long as the vector expresses a target gene in a variety of host cells including prokaryotes and eukaryotes, and functions to produce a target protein. However, a vector capable of mass-producing a foreign protein in a form similar to a native form while possessing a strong promoter to achieve strong expression of the target protein is preferred. The recombinant vector preferably contains at least a promoter, a start codon, a gene encoding a target protein, a stop codon and a terminator. The recombinant vector may further suitably contain DNA coding a signal peptide, an enhancer sequence, 5'- and 3'-untranslational regions of a target gene, a selection marker region, a replication unit, or the like.

The second step is to transform a host cell with the recombinant vector and culture the host cell. The recombinant vector is introduced into a host cell to generate a transformant by a method described by Sambrook, J. et al., Molecular Cloning, A Laboratory Manual (2nd Ed.), Cold Spring Harbor Laboratory, 1. 74, 1989, the method including a calcium phosphate or calcium chloride/rubidium chloride method, electroporation, electroinjection, chemical treatments such as PEG treatment, and gene gun. A useful protein can be produced and isolated on large scale by culturing a transformant expressing the recombinant vector in a nutrient medium. Common media and culture conditions may be suitably selected according to host cells. Culture conditions, including temperature, pH of a medium and culture time, should be maintained suitably for a cell growth and mass production of a protein of interest. Host cells capable of being transformed with the recombinant vector according to the present invention include both prokaryotes and eukaryotes. Host cells having high introduction efficiency of DNA and having high expression levels of an introduced DNA may be typically used. Examples of host cells include known prokaryotic and eukaryotic cells such as *Escherichia* sp., *Pseudomonas* sp., *Bacillus* sp., *Steptomyces* sp., fungi and yeast, insect cells such as *Spodoptera frugiperda* 9 (Sf9), and animal cells such as CHO, COS 1, COS 7, BSC 1, BSC 40 and BMT 10. *E. coli* may be preferably used.

The third step is to induce expression as well as accumulation by the fusion protein. In the present invention, the inducer IPTG was used for the induction of peptide expression, and induction time was adjusted to obtain maxmimal protein yield.

The final step is to isolate and purify the fusion protein. Typically, a recombinantly produced peptide can be recovered from a medium or a cell lysate. When the peptide is in a membrane-bound form, it may be liberated from the membrane using a suitable surfactant solution (e.g., Triton-X 100) or by enzymatic cleavage. Cells used in the expression of the fusion protein may be destroyed by a variety of physical or chemical means, such as repeated freezing and thawing, sonication, mechanical disruption or a cell disrupting agent, and the fusion protein may be isolated and purified by commonly used biochemical isolation techniques (Sambrook et al., Molecular Cloning: A laboratory Manual, 2nd Ed., Cold Spring Harbor Laboratory Press, 1989; Deuscher, M., Guide to Protein Purification Methods Enzymology, Vol. 182. Academic Press. Inc., San Diego, Calif., 1990). Non-limiting examples of the biochemical isolation techniques include electrophoresis, centrifugation, gel filtration, precipitation, dialysis, chromatography (ion-exchange chromatography, affinity chromatography, immunosorbent affinity chromatography, reverse phased HPLC, gel permeation HPLC), isoelectric focusing, and variations and combinations thereof.

Protein A consists of five domains (D, E, A, B, and C) which bind to Fc region of immunoglobulin G. The present inventor constructed a novel immobilizing linker protein, in *Escherichia coli* by genetically fusing mussel adhesive protein (MAP) with two domains (B and C) of protein A for efficient immobilization of antibodies on diverse surfaces. BC domain without MAP was also biosynthesized as a comparative control (FIG. 1).

Based on direct surface coating analyses with color imaging, it was found that BC-MAP successfully was coated on diverse surfaces including glass slide, polypropylene, and titanium while BC domain alone exhibited partial coating.

Figure 3:
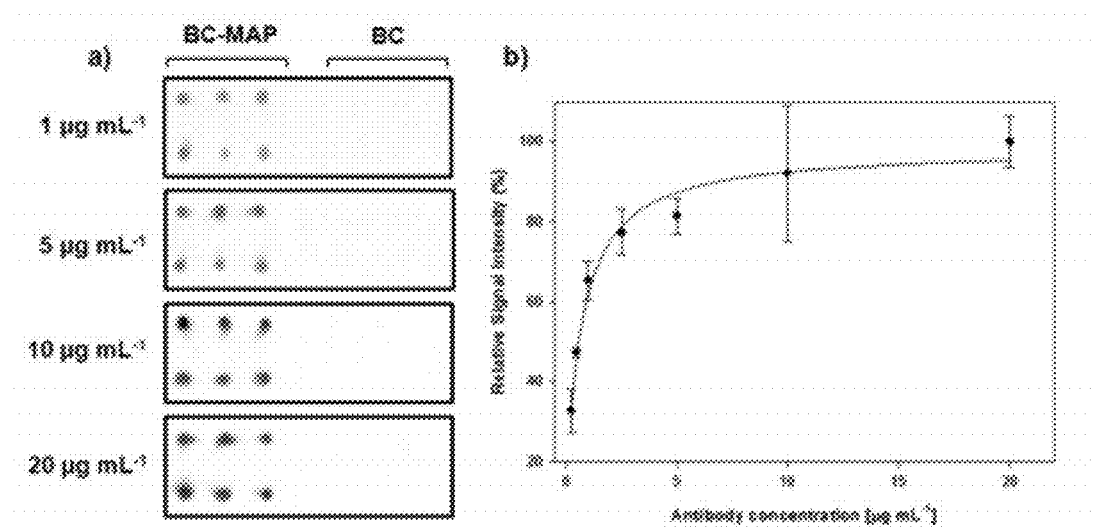
FIG. 3(a) shows color image analysis depending on immobilized alkaline phosphatase-conjugated anti-rabbit IgG concentration on glass slide coated by BC-MAP and BC.
FIG. 3(b) shows color signal intensities are plotted in the bottom graph. Each value and error bar represents the mean of six independent spots and its standard deviation.
Figure 4:
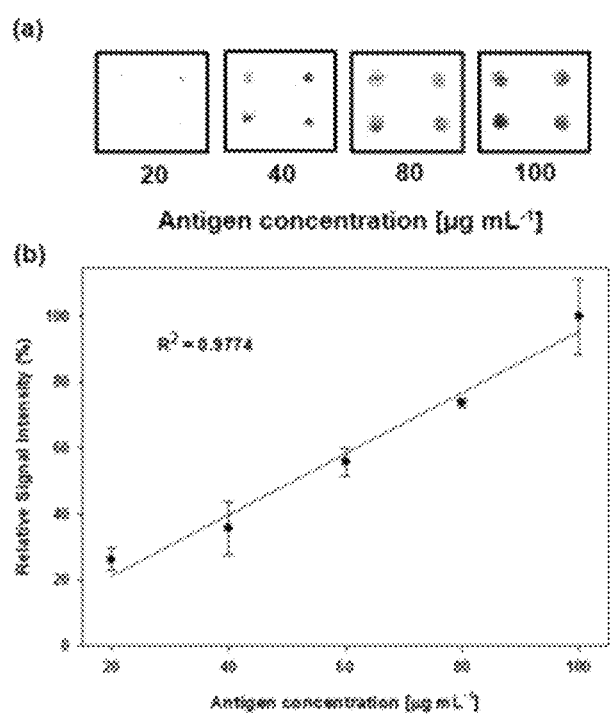
FIG. 4(a) shows color images of anti-alkaline phosphatase functionalized glass slide coated by BC-MAP response to different concentrations of alkaline phosphatase. 100 μg $mL^{-1}$ anti-alkaline phosphatase was used.
FIG. 4(b) shows color signal intensities are plotted in bottom graph. Each value and error bar represents the mean of six independent spots and its standard deviation.
Figure 5:
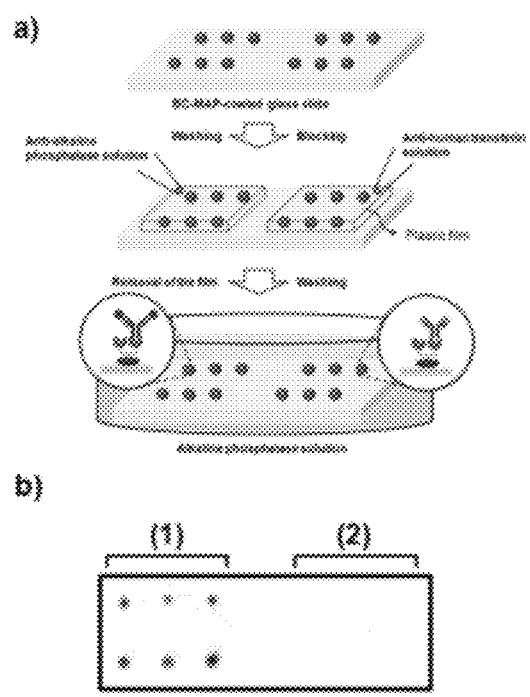
FIG. 5(a) shows schematic procedure to investigate the specificity of antibodies functionalized glass slide coated by BC-MAP.
FIG. 5(b) Specificity of antibodies functionalized glass slide coated by BC-MAP. Antibodies for alkaline phosphatase (1) and transferrin (2) were added onto each defined region of BC-MAP-coated glass slide and the slide was reacted with sample containing alkaline phosphatase.

Importantly, antibody was efficiently immobilized on BC-MAP-coated surfaces, and immobilized antibody interacted selectively with the corresponding antigen (FIG. 3 to FIG. 5).

Figure 6:
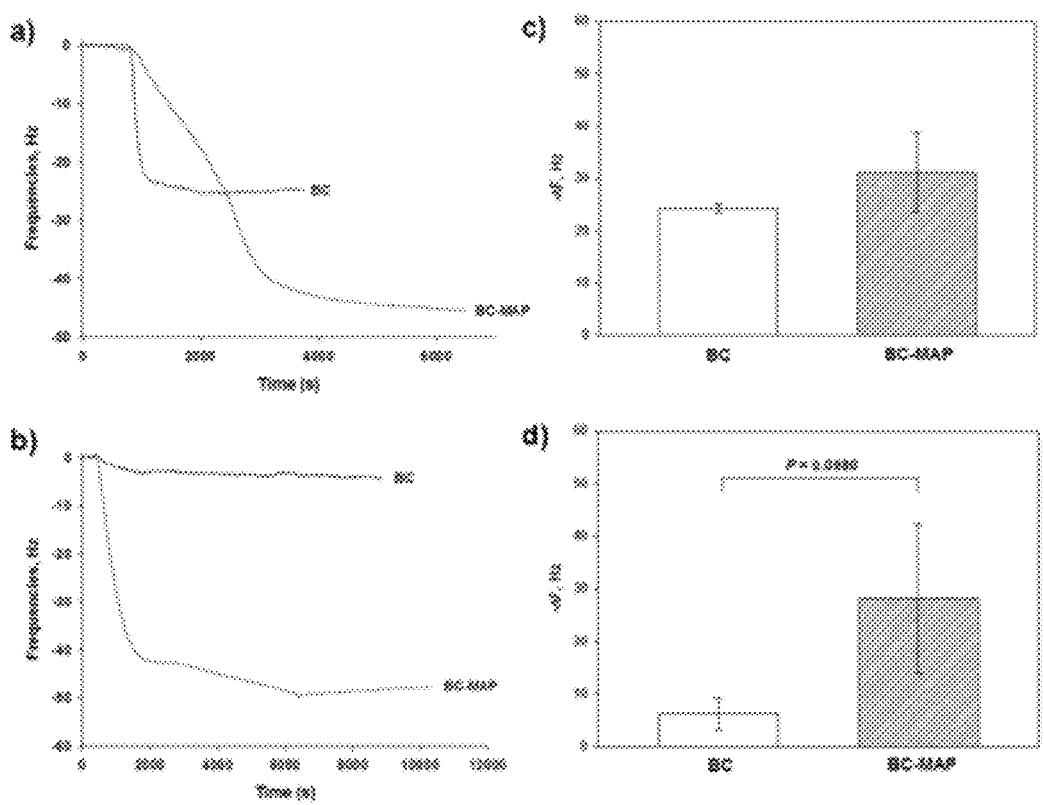
FIG. 6(a) shows QCM response for the binding of BC and BC-MAP on gold at flow rate 10 μL min$^{-1}$.
FIG. 6(b) shows QCM response for the binding of antibody on BC- and BC-MAP-coated gold at a flow rate of 10 μL min$^{-1}$.
FIG. 6(c) shows data analysis of frequency shift upon the binding of BC and BC-MAP on gold at a flow rate of 10 μL min$^{-1}$. Values are the means from three independent experiments. Standard derivations are indicated in bar graphs.
FIG. 6(d) shows data analysis of frequency shift upon the binding of antibody on BC- and BC-MAP-coated gold at a flow rate of 10 μL min$^{-1}$. Values are the means from three independent experiments. Standard derivations are indicated in bar graphs.
Figure 7:
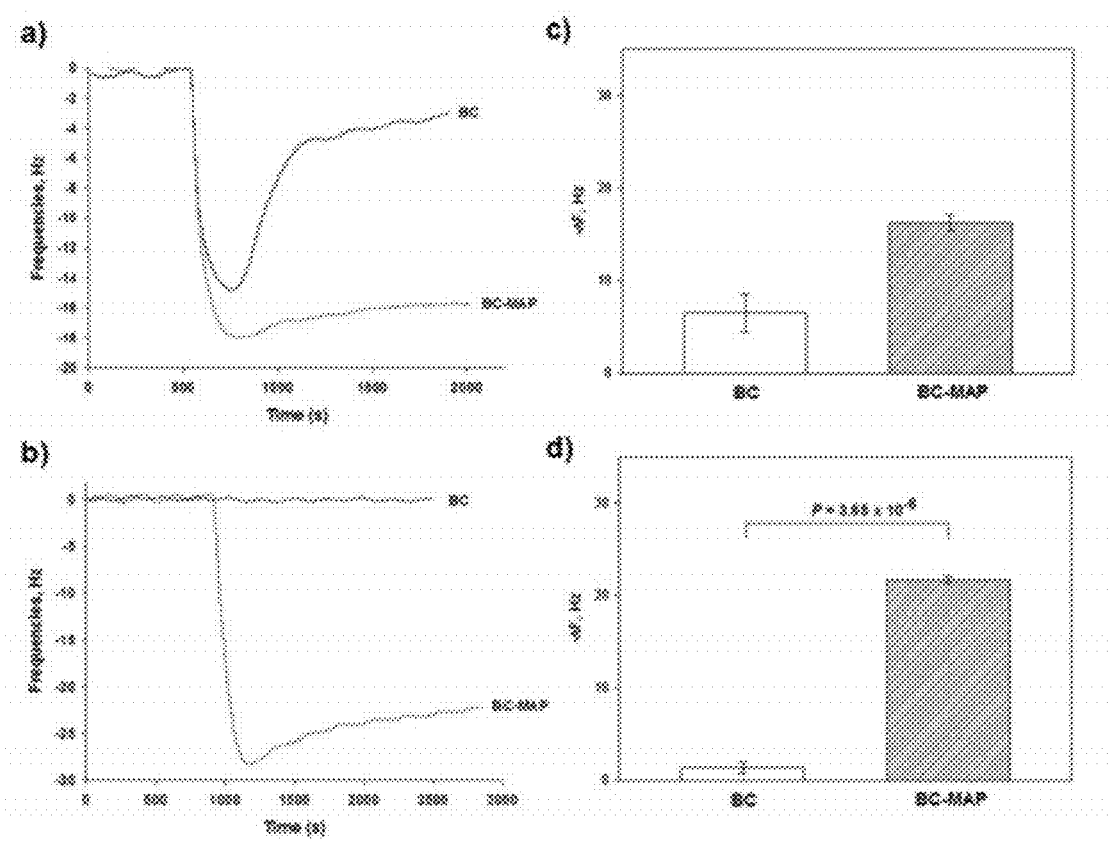
Figure 8:
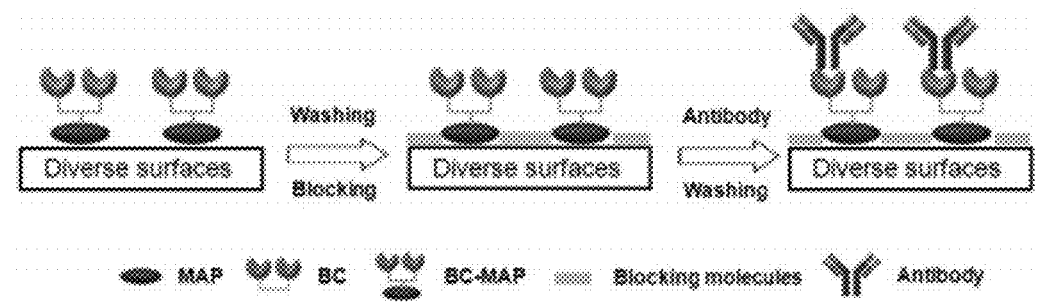
FIG. 8 shows schematic representation of antibody immobilization on diverse surfaces coated by BC-MAP.

Quartz crystal microbalance (QCM) analyses showed that BC-MAP has an excellent antibody binding ability compared to BC protein on the gold surface. These results demonstrated that unique strong and underwater adhesive properties of MAP, which can promote a direct and efficient immobilization of BC-MAP molecules on diverse surfaces without any additional surface treatments (FIG. 6 and FIG. 7). Thus, the proposed BC-MAP fusion protein could be a valuable linker material to facilitate an efficient immobilization of antibodies onto diverse solid supports.

In yet another aspect, the present invention relates to a biochip comprising a solid substrate to which the fusion protein is attached.

The biochip comprises a suitable solid substrate to which the fusion protein is attached. Protein A or a peptide derived from protein A can afford oriented antibody immobilization on surfaces of the solid substrate by binding Fc region of the antibody. MAP or a peptide derived from MAP can attach to a variety of surfaces and therefore, the fusion protein can attach to various surfaces of the solid substrate as well without loss of activity.

"Substrate" or "solid support" or other grammatical equivalents used herein refer to any materials that can be modified to contain discrete individual sites appropriate for the attachment or association of the antibody and is amenable to at least one detection method. As will be appreciated by those in the art, the number of possible substrates are extensive, and include, but are not limited to, glass and modified or functionalized glass, plastics (including acrylic, polystyrene and copolymers of styrene and other materials, polypropylene, polyethylene, polybutylene, polyurethanes, Teflon, tetrafluoroethylene, etc.), polysaccharides, nylon or nitrocellulose, resins, silica or silica-based materials including silicon and modified silicon, carbon, metals, inorganic glasses, etc. In general, the substrates allow optical detection and do not appreciably fluorescence.

The substrate provides a place for antigen-antibody interactions as well as functions as a solid support. The size or shape of the substrate and sites of immobilizing antibody on the substrate would be diverse according to the purpose of the analysis or apparatus such as spotting machine or scanner.

In another aspect, the present invention relates to a method for detecting antigen in a biological sample using the biochip.

Preferably, the detecting method of the present invention comprises the step of immobilizing an antibody which specifically binds to the target antigen on the solid substrate of the biochip, adding a biological sample comprising the target antigen to the biochip, and detecting the target antigen by measuring antigen-antibody interactions.

The first step is to immobilize an antibody which specifically binds to the target antigen on the solid substrate of the biochip. In the present invention, an antibody is fixed to a solid substrate by the fusion protein to facilitate washing and isolation of the antigen-antibody complex. In the fusion protein, protein A or a peptide derived from protein A can afford oriented antibody immobilization on the solid substrate by binding Fc region of the antibody, and MAP can attach to a variety of surfaces. Therefore, the fusion protein can attach to various solid substrates as well without loss of activity.

The term "antibody" refers to an immunoglobulin molecule having a specific structure that binds specifically to a molecule comprising the antigen used for synthesizing the antibody or with an antigen closely related to it. As used herein, the term "antibody" broadly includes full length antibodies and may also include certain antibody fragments thereof. Also included are monoclonal and polyclonal antibodies, multivalent and monovalent antibodies, multispecific antibodies (for example bi-specific antibodies), chimeric antibodies, human antibodies, and humanized antibodies.

As used herein, an "antigen-binding fragment" or "antibody fragment" means a portion of the intact antibody that preferably retains most or all, or minimally at least one of, the normal functions of that antibody fragment. An antibody fragment, for example, may comprise an Fc region that retains all or most or some of the functions of the corresponding Fc region in the intact antibody. Examples of antibody fragments include Fab, Fab', F(ab')$_2$ and Fv fragments, linear antibodies, diabodies, single chain antibodies (ScFV) and multispecific antibodies.

As used herein, a "monoclonal antibody" means an antibody that is a highly specific antibody directed against a single target antigen. A monoclonal antibody may be obtained from a population of homogenous or substantially homogenous antibodies wherein each monoclonal antibody is identical and/or bind the same epitope, except for natural mutations which may occur in minor amounts.

The second step is to add a biological sample comprising the target antigen to the biochip.

Biological sample as used herein means any sample derived from a subject to be detected. The sample may be any sample known in the art in which the target antigen can be detected by antigen-antibody interactions. Included are any body fluids such as plasma, blood, saliva, interstitial fluid, serum, urine, synovial, cerebrospinal, lymph, seminal, amniotic, pericardial fluid and ascites, but not limited thereto.

The term "target antigen" as used herein refers to any solid or non-solid material capable of binding to an antibody immobilized on the biochip or a fragment or variant thereof. In one embodiment the term refers to any natural or non-natural molecule that binds to an antibody immobilized on the biochip or a fragment or variant thereof. Examples of target antigen include proteins, peptides, carbohydrates, lipids, and small molecule compounds, but not limited thereto.

The third step is to detect the target antigen by measuring antigen-antibody interactions.

To facilitate detection, antibodies and fragments herein may be labelled with detectable markers such as fluorescent, bioluminescent, and chemiluminescent compounds, as well as radioisotopes, magnetic beads and affinity labels (e.g biotin and avidin). Examples of labels which permit indirect measurement of binding include enzymes where the substrate may provide for a coloured fluorescent product. Suitable enzymes include horseradish peroxidase, alkaline phosphatase, malate dehydrogenase and the like. Fluorochromes (e.g Texas Red, fluorescein, phycobiliproteins, and phycoerythrin) can be used with a fluorescence activated cell sorter. Labelling techniques well known in the art can be utilized.

An antigen-antibody interaction can be detected by any means known in the art. Most commonly, antigen-antibody interactions herein are detected using an assay such as ELISA or RIA, competitive binding assays, sandwich assays, non-competitive assays, fluoroimmunoassay, immunofluorometric assay, or immunoradiometric assays, luminescence assays, or chemiluniescence assays.

The present invention is further explained in more detail with reference to the following examples. These examples, however, should not be interpreted as limiting the scope of the present invention in any manner.

Example 1

Construction of Expression Vectors 1.1: Construction of Expression Vector for BC-MAP Fusion Protein The gene coding of MAP fp-5 was amplified by a polymerase chain reaction (PCR) from the previously constructed vector pMDG05. The forward primer (F1: 5'-GGGC-CCATGGGGTGGCGGAGGGAGCTCTGAA-GAATATAAAG-3', SEQ ID No:1) was designed to contain a NcoI restriction enzyme site and the sequence encoding a GGGG amino acid linker. The backward primer (B1: 5'-CGCGCTCGAGGCTGCTGCCGCCAT-AATATTTTTTATAG-3', SEQ ID No:2) was designed to contain a XhoI restriction enzyme site. The PCR product was digested with two restriction enzymes of NcoI and XhoI (Fermentas, Burlington, Ontario, Canada). The digested DNA fragment was ligated with a pET22b(+) vector (Novagen, San Diego, Calif., USA), which predigested with NcoI and XhoI, by using a ligation kit (TaKaRa, Shiga, Japan) to make the plasmid pET-MAP. The gene, encoding two domains (B and C domain) of protein A, was amplified by PCR from the genomic DNA of *Staphylococcus aureus* ATCC 6538 (B. H. Hwang, H. J. Cha, *Biotechnol. Bioeng.* 2010, 106, 183). The forward primer (F2: 5'-GCGC-CATATGGATAACAAATTCAACAAAGAACAAC-3', SEQ ID No:3) was designed to contain a NdeI restriction enzyme site and the backward primer (B2: 5'-GCGCCCATG-GTTTTGGTGCTTGAGCATCGTTTAGC-3', SEQ ID No:4) was designed to contain a NcoI restriction enzyme site. The PCR product was digested with two restriction enzymes of NdeI (Fermentas, Burlington, Ontario, Canada) and NcoI. The digested PCR was liageted with pET-MAP, which predigested with NdeI and NcoI, resulting in the plasmid pET-BC-MAP (FIG. 2(a))

1.2: Construction of Expression Vector for Sole BC Protein

For the construction of BC protein as control protein, the corresponding gene was amplified by PCR with the forward primer (F2) and backward primer (B3: 5'-GCGCCTC-GAGTTTTGGTGCTTGAGCATCGTTTAGC-3', SEQ ID No:5). The PCR product was ligated into the NdeI and XhoI sites of pET22b(+) to make pET-BC (FIG. 2a).

Example 2

Expression and Purification of BC-MAP and Sole BC Proteins

Each plasmid containing pET-BC-MAP or pET-BC was transformed into *Escherichia coli* BL21 (DE3). The transformants were grown to 0.8-0.9 $OD_{600}$ at 37° C. in shake flasks containing of 400 mL of Luria-Bertani (LB) medium (0.5% yeast extract, 1% tryptophan, and 1% NaCl) with 50 µg $mL^{-1}$ ampicillin. The expression was induced by adding isopropyl β-D-thiogalactopyranoside (IPTG) to a final concentration of 1 mM. The transformed cells were grown for an additional 10 h at 37° C. The cells were harvested by centrifugation at 4000 g for 10 min. The cell pellets were resuspended in lysis buffer (50 mM NaH2PO4, 300 mM NaCl, 10 mM imidazole, pH 8.0) and disrupted with a sonic dismembrator (Fisher scientific, USA) for 10 min at 50% power (3 sec pulse on and 2 sec pulse off). The soluble and insoluble fractions were then separated by centrifugation at 9000 g for 30 min at 4° C. The soluble fractions were loaded into a Ni-NTA column (Qiagen, Valencia, Calif., USA). BC and BC-MAP were eluted with elution buffer (50 mM NaH2PO4, 300 mM NaCl, 250 mM imidazole, pH 8.0) and desalted by a PD-10 column (GE Healthcare, Sweden). The protein concentration was determined by Bradford method using bovine serum albumin (BSA) (Sigma-Aldrich, St. Louis, Mo., USA) as a standard.

Example 3

MALDI-TOF MS Analysis

Matrix-assisted laser desorption ionization mass spectrometry with time-of-flight (MALDI-TOF MS) analysis was performed on a 4700 Proteomics Analyzer (AB Sciex) in the positive ion linear mode. A-cyano-4-hydroxycinnamic acid in 50% acetonitrile and 0.1% trifluoroacetic acid was used as the matrix solution. Sample were diluted 1:20 with matrix solution, and 1 µL of the mixture was spotted onto the MALDI sample target plates and evaporated using a vacuum pump. Spectra were obtained in the mass range between 5,000 and 25,000 Da with ~2000 laser shots. Internal calibration was performed using mix 3 of sequazyme peptide mass standard kit (AB Sciex).

Example 4

Direct Surface Coating Analysis

Three types of surfaces (glass (Marienfeld GmbH & Co., Lauda-Königshofen, Germany), titanium (Alfa Aesar, Ward Hill, Mass., USA), and polypropylene) were used for direct surface coating analyses. Glass slide was cleaned with hot piranha solution (10% (v/v) $H_2O_2$, 30% (v/v) $H_2SO_4$) and was thoroughly rinsed with ethanol and $dH_2O$. Titanium was treated with 40% sulfuric acid at room temperature for 15 min and rinsed extensively with $dH_2O$. And then, the titanium was boiled in dH2O and washed with dH2O and acetone. The titanium was dried under $N_2$ gas. BC-MAP (2 mg $mL^{-1}$) and BC (2 mg $mL^{-1}$) were coated on each surface and the surfaces were dried for complete immobilization. After washing with PBS (pH 7.5) at 200 rpm shaker for 5 min, the surfaces was treated with 5% non-fat milk solution for 1 h at room temperature, followed by washing with TTBS (20 mM Tris-HCl, 500 mM NaCl, 0.0005% Tween 20 (pH 7.5)) (5 min×3 times). Anti-rabbit antibody conjugated with alkaline phosphatase solution (as a target antibody) (Sigma-Aldrich) was added onto BC-MAP-coated surfaces for 1 h at room temperature. To analyze antibody-binding capability of BC-MAP on the surfaces, antibody-immobilized surfaces were treated with NBT/BCIP solution (Bio Basic Inc., Canada) for 20 min after washing with sequencial TTBS (5 min×2 times) and TBS (20 mM Tris-HCl, 500 mM NaCl (pH 7.5)) (5 min×1 time).

For analyzing immobilizing degree on BC-MAP-coated glass slide according to antibody concentrations, various antibody concentrations (20 µg $mL^{-1}$-200 ng $mL^{-1}$) were used.

Example 5

Antigen-Antibody Interaction on BC-MAP-Coated Glass Slide

BC-MAP- and BC-coated glass slides were constructed as described above. The glass slide was immersed onto anti-alkaline phosphatase (Sigma-Aldrich) solution (100 µg $mL^{-1}$), followed by washing with TTBS (5 min×3). Alkaline phosphatase (antigen) solutions with different concentrations (100, 80, 60, 40, 20, and 10 µg $mL^{-1}$) were added onto the antibody immobilized surface for 1 h at room temperature.

After washing as described above, the surface was reacted with NBT/BCIP solution for 1 h

Example 6

Selectivity of Antibodies Functionalized BC-MAP-Coated Glass Slide

BC-MAP-coated glass slide was constructed (FIG. 5c). After washing and blocking, antibody solutions (anti-alkaline phosphatase and anti-human transferin (Sigma-Aldrich), 2 mg mL$^{-1}$) were added onto each defined block by Gene Frame® (Thermo Scientific, San Jose, Calif., USA) and then the glass slide was immersed with alkaline phosphatase solution (100 μg mL$^{-1}$) after washing with sequencial TTBS/TBS. Color development processes were performed by same procedure described above except reaction time (90 min) with NBT/BCIP solution.

Example 7

Quartz Crystal Microbalance (QCM) Analysis

Gold-coated quartz crystals (5 MHz, Stanford Research System, Sunnyvale, Calif., USA) were cleaned by UV irradiation for 20 min before a syringe pump (WPI, Sarasota, Fla., USA) equipped with a low-pressure liquid chromatography injector valve and a 250 μL injection loop (Upchurch Scientific, Oak Harbor, Wash., USA) was used to inject either sample solution or carrier solution (1×PBS, pH 7.4) into the flow cell at a flow rate of 10 or 50 μL min$^{-1}$. After rinsing with DW and drying with ultra-high purity N$_2$, the crystals were mounted inside QCM flow modules. PBS (1×) was then injected into the flow module until stable baseline f shifts were achieved. A total of 250 μL of BC-MAP (0.2 mg mL$^{-1}$), BC (0.12 mg mL$^{-1}$), or MAP (0.2 mg mL$^{-1}$) was injected into the flow module for attachment to the gold surface. After rinsing with PBS until the frequency shift was stable, the surface was treated with 250 μL BSA solution (1 mg mL$^{-1}$) to block non-specific interactions. This step was followed by a PBS rinse to remove unattached BSA. Then 250 μL of polyclonal anti-DsRed antibody solution (20 ng mL$^{-1}$; Santa Cruz Biotechnology, Santa Cruz, Calif., USA) was injected into the flow module. The adsorbed mass was calculated using the Sauerbrey equation (1):

$$\Delta f = -\frac{2 f_0^2}{A \sqrt{\rho_q \mu_q}} \Delta m \quad (1)$$

where $\Delta f$ is the change in fundamental frequency of the coated crystal, $f_0$ is the resonant frequency of the unloaded crystal (5 MHz), A is the active area of the crystal between electrodes (1.267 cm$^2$), $\rho_q$ is the density of quartz (2.648 g cm$^{-3}$), $\mu_q$ is the shear modulus of quartz (2.947×10$^{11}$ g cm$^{-1}$ s$^{-2}$), and $\Delta m$ is the change in mass per unit surface area.

Experimental Example 1

Expression and Purification of BC-MAP and BC

Protein A consists of five domains (D, E, A, B, and C) which bind to Fc region of immunoglobulin G (IgG). We constructed novel immobilizing linker by fusion of BC domain of protein A with MAP. BC domain without MAP was also constructed as a comparative control. To produce recombinant BC-MAP and sole BC in E. coli, each BC-MAP and BC gene was cloned into expression vector containing His$_6$ affinity purification tag sequence and an inducible T7 promoter (FIG. 1a). Both BC-MAP and BC were majorly expressed as soluble form in E. coli (data not shown).

To investigate potential activity of BC-MAP as immobilizing agent for efficient immobilization of antibodies on diverse surfaces, recombinant BC-MAP and BC proteins were purified by immobilized metal affinity chromatography (IMAC). Each actual molecular weight of BC-MAP and BC from sodium dodecyl sulfate polyacrylamide gel electrophoresis (SDS-PAGE; FIG. 1b) and matrix-assisted laser desorption/ionization-time of flight mass spectrometry (MALDI/TOF-MS) was similar to the calculated molecular weight of ~23.5 kDa and ~14.2 kDa, respectively. Finally, we obtained high purity of BC-MAP (~90.7%) and BC (~97.0%) by one-step affinity purification (FIG. 1b).

Experimental Example 2

Antibody Immobilization on BC-MAP-Coated Surfaces

In order to investigate antibody-immobilizing activity of BC-MAP, we performed direct coatings on diverse surfaces with color image analysis. We used three different surfaces (glass slide, titanium, and polypropylene) and anti-rabbit IgG conjugated with alkaline phosphatase as a model antibody. Glass slide, polymer, and titanium have been utilized as solid supports for protein arrays as well as immunosensors. Sole BC protein was used a comparative control. First, BC-MAP- and BC-coated surfaces were severely washed with PBS at 200 rpm shaker by changing washing time (5, 10, and 15 min) to analyze coated pattern along with washing time. After washing, the surfaces were stained using Coomassie blue. When the surfaces were washed for 5 min, sole BC was completely disappeared on all surfaces. However, most BC-MAP was not removed on all surfaces under 15 min washing time (data not shown). Note that sole BC was removed on the surfaces even under gentle washing condition (data not shown). This implies that surface binding of BC-MAP is much more stable and stronger than interaction between BC and the surfaces owing to the unique property of MAP. This result was consistent with our previous result that MAP have strong binding ability to diverse surfaces such as glass slide, poly(methyl methacrylate) plate, polystyrene plate, and aluminum. Using this adhesive characteristic of MAP, BC-MAP could be used as immobilizing agent for efficient immobilization of antibody on diverse surfaces without any additional steps. In the subsequent experiments, we set washing time as 5 min for protein coating.

Figure 2:
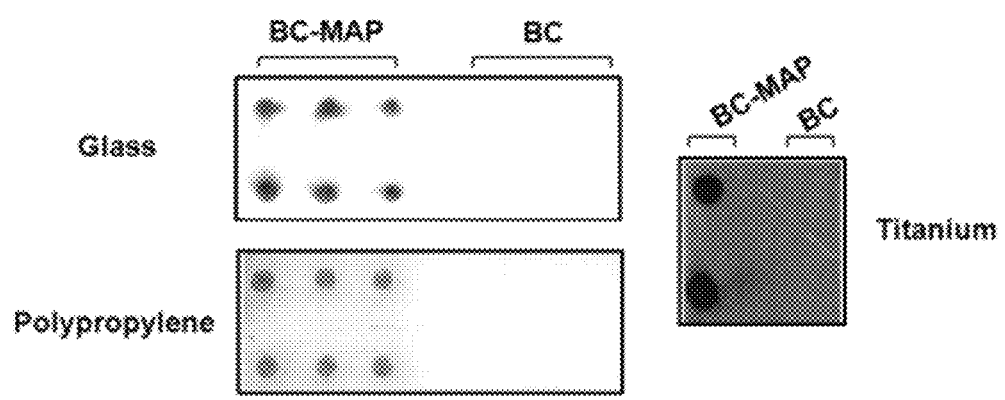
FIG. 2 shows direct coatings of BC-MAP and sole BC with color image analyses on diverse surfaces. Alkaline phosphatase-conjugated anti-rabbit IgG was used as a model antibody.

After washing and blocking by 5% non-fat milk, BC-MAP-coated the surfaces was immerged in antibody solution, followed by washing with TTBS/TBS buffer solution and reacting with NBT/BCIP solution. As expected, the model antibody, anti-rabbit IgG, was sucessfully immobilized on all three BC-MAP-coated surfaces (FIG. 2). This result indicates that BC-MAP-based immobilization of antibody onto diverse surfaces does not require any additional steps including chemical modification and BC domain of BC-MAP interacts specifically with Fc region of IgG through proper orientation of BC-MAP through binding of MAP domain onto surfaces and exposure of BC domain toward IgG-containing solution. If BC domain of BC-MAP was immobilized on surfaces but not exposed outward, surface-immobilized BC-MAP would be easily removed during washing step. Thus, MAP domain of BC-MAP played a critical role for facile antibody immobilization on diverse surfaces and exposure of functional BC domain.

Experimental Example 3

Antigen-Antibody Interaction on BC-MAP-Coated Glass Slide

In diagnosis, quantitative analysis is one of important issues. Thus, before analyzing antigen-antibody interaction on BC-MAP-coated surface, we investigated immobilization degree according to antibody concentrations. Among three surfaces, glass slide was used in further subsequent experiments because it is commonly utilized as solid surface in antibody array. While the spot shapes on hydrophobic polypropylene were somewhat clean, the shapes on glass slide were not relatively uniform because hydrophilic surface leads to larger printed spots. FIG. 3 shows antibody-BC-MAP interaction in a range of antibody concentrations from 200 ng mL$^{-1}$ to 20 μg mL$^{-1}$. We found that the relative signal intensities of color spots increased according to applied antibody concentrations (FIG. 3a). We determined that detection limit and saturation point were corresponded to 200 ng mL$^{-1}$ and 10 μg mL$^{-1}$, respectively, at 20 min fixed color development time (FIG. 3b).

Next, we used anti-alkaline phosphatase IgG as a model antibody and alkaline phosphatase as a model antigen to investigate interaction of the immobilized antibody on BC-MAP-coated glass slide with the corresponding antigen and potency of quantitative analysis. Alkaline phosphatase solutions with different concentrations were applied on the anti-alkaline phosphatase IgG-immobilized BC-MAP-coated glass slide. As shown in FIG. 4, the signal intensities increased along with increasing antigen concentrations. With considering background intensity value (11.18±1.70) on bare glass slide and fixed color development time, we found that at least 20 μg mL$^{-1}$ antigen could be detected on the glass slide. Importantly, linear correlation between signal intensity and antigen concentration was shown with high coefficient of determination ($R^2$) of over 0.97 at the range of 20-100 μg mL$^{-1}$ antigen concentration (FIG. 4b). The result indicates that antibody array using BC-MAP as immobilizing agent can be used for quantitative analysis of antigen-antibody interaction. Furthermore, the selectivity of this BC-MAP-based immunosensor system was investigated by loading two antibody solutions (anti-alkaline phosphatase IgG as a positive antibody and human transferrin IgG as a negative control) onto each defined blocks and then reacting with alkaline phosphatase solution (FIG. 5a). FIG. 5b shows that the antibody array using BC-MAP linker was very specific to the corresponding antigen without detection of cross-reaction, demonstrating the good selectivity of the system.

Experimental Example 4

QCM Analysis of BC-MAP Material

We also investigated the function of BC-MAP as a linker molecule for efficient immobilization of antibody using quartz crystal microbalance (QCM). We examined the ability of BC-MAP at two different conditions. First, BC-MAP was tested at relatively low flow rate on bare gold surface. Second, relatively high flow rate was used to identify markedly the capability of BC-MAP although it was reported that conventional QCM design in which a circular resonator is sandwiched between two O-rings shows unstable signal at high flow rate. BC-MAP and sole BC (control) were immobilized on the gold surfaces, and anti-DsRed antibodies were applied on BC-MAP- and BC-coated gold surfaces, respectively. QCM plots for the binding events between protein and gold and between antibody and protein are shown in FIGS. 6a-b and FIG. 7a-b, respectively, under two different conditions. FIG. 6a and FIG. 7a shows QCM response for the binding of BC-MAP and sole BC onto gold surfaces at 10 μL min$^{-1}$ and 50 μL min$^{-1}$, respectively. FIG. 6b and FIG. 7b represents QCM response for the binding of anti-DsRed antibody onto BC-MAP- and BC-coated gold surfaces at 10 μL min$^{-1}$ and 50 μL min$^{-1}$, respectively. We compared QCM responses upon the bindings of BC-MAP and BC on gold surfaces (FIG. 6c & FIG. 7c). At the 10 μL min$^{-1}$ flow rate condition, the changed frequency values of BC and BC-MAP on gold were 24.0±0.9 and 31.1±7.6 Hz, which corresponded to the similar bindings of $1.8 \times 10^{13}$ and $1.4 \times 10^{13}$ molecules cm$^{-2}$ on the surface, respectively (Table 1). Different with the result of direct surface coating analysis, sole BC also showed a similar binding level with BC-MAP on gold surface in QCM system. This was resulted from smooth washing condition (relatively low flow rate) used in QCM system. At the higher flow rate condition (50 μL min$^{-1}$), the frequency shift values of BC and BC-MAP on gold were 6.5±2.0 and 16.2±0.8 Hz, indicating about 73% and 47% decreases of these on gold at low flow rate, respectively (Table 1). We confirmed that binding of BC-MAP on gold surface was more stable and stronger than that of sole BC.

TABLE 1

| Flow rate [μL min$^{-1}$] | Sample | Protein immobilization [Hz] | Surface density [molecule cm$^{-2}$] | Antibody binding [Hz] | Surface density [molecule cm$^{-2}$] | Binding efficiency [%] |
|---|---|---|---|---|---|---|
| 10 | BC | 24.0 ± 0.9 | $1.8 \times 10^{13}$ | 6.1 ± 3.0 | $4.3 \times 10^{11}$ | 2.4 |
|  | BC-MAP | 31.1 ± 7.6 | $1.4 \times 10^{13}$ | 28.2 ± 14.1 | $2.0 \times 10^{12}$ | 14.2 |
| 50 | BC | 6.5 ± 2.0 | $4.9 \times 10^{12}$ | 1.4 ± 0.6 | $9.9 \times 10^{10}$ | 2.0 |
|  | BC-MAP | 16.2 ± 0.8 | $7.3 \times 10^{12}$ | 21.7 ± 0.5 | $1.5 \times 10^{12}$ | 20.5 |

Next, we compared QCM responses upon the bindings of antibody on BC-MAP and sole BC-coated gold surfaces (FIG. 6d & FIG. 7d). Nonspecific interactions were blocked by treatment of BSA before addition of anti-DsRed antibody. At the lower flow rate condition 10 μL min$^{-1}$, the antibody binding signal to BC-MAP-coated gold surface was 28.2±14.1 Hz, whereas the value to BC-coated gold surface was 6.1±3.0 Hz (Table 1). By considering the molecular weights and the mass changes due to adsorption (Δm) of the antibody (150 kDa), BC-MAP (23.5 kDa), and BC (14.2 kDa), we determined that BC-coated gold surface had only 2.4% of immobilized BC which was involved in interaction with the Fc region of antibody (Table 1). We suspect that active binding sites of BC were not exposed toward the antibody solution due to non-oriented physical adsorption on gold surface. Importantly, over 14.2% of immobilized BC-MAP interacted with the antibody on gold surface and this was about 6-fold more antibody binding compared to the sole BC molecule. At the higher flow rate (50 µL min$^{-1}$), the antibody binding signals to sole BC- and BC-MAP-coated gold surfaces were 1.4±0.6 and 21.7±0.5 Hz, respectively (Table 1). As a result, the BC-MAP showed increase of binding efficiency of 20.5% while the binding efficiency of sole BC maintained at similar low level of ~2.0% (Table 1). We speculated that this is because BC domain of BC-MAP on gold at high flow rate well exposed the antibody solution compared this on gold at low flow rate by immobilizing MAP domain of BC-MAP onto the surface but preventing BC domain of BC-MAP from interacting with the surface. Two explanations might be possible for higher antibody binding efficiency of BC-MAP. First, active binding sites of BC domain in BC-MAP molecule were effectively exposed outward. Second is that MAP domain in BC-MAP was also involved in antibody binding. To investigate possibility for direct involvement of MAP in antibidy binding, we performed antibody binding on sole MAP-coated gold surface. But, we found that MAP was not involved in antibody binding after BSA blocking although much larger quantity of MAP was used. Thus, we can exclude the possibility about direct involvement of MAP in antibidy binding and conclude that BC-MAP binds to surface with oriented manner for BC domain.

What is claimed is:

1. A fusion protein comprising protein A or a peptide derived from protein A and a mussel adhesive protein or a peptide derived from a mussel adhesive protein.

2. The fusion protein according to claim 1, wherein the peptide derived from a mussel adhesive protein is a protein, a fragment or a fusion peptide of at least one selected from group consisting of mussel foot protein (FP)-1, FP-2, FP-3, FP-4, FP-5 and FP-6.

3. The fusion protein according to claim 2, wherein the peptide derived from a mussel adhesive protein is FP-5 having an amino acid sequence of SEQ ID No: 6.

4. The fusion protein according to claim 1, wherein the protein A has an amino acid sequence of SEQ ID No: 7.

5. The fusion protein according to claim 1, wherein the peptide derived from protein A comprises 50 to 500 continuous amino acid residues of amino acid sequence of SEQ ID No:7.

6. The fusion protein according to claim 1, wherein the peptide derived from protein A is a protein, a fragment, and a fusion peptide of at least one selected from the group consisting of domain A, domain B, domain C, domain D, domain E, and BC domain of the protein A.

7. The fusion protein according to claim 6, wherein the peptide derived from protein A is a protein, a fragment, and a fusion peptide of at least one selected group from the domain A having an amino acid sequence of SEQ ID No: 8, domain B having an amino acid sequence of SEQ ID No:9, domain C having an amino acid sequence of SEQ ID No: 10, domain D having an amino acid sequence of SEQ ID No: 11 and domain E having an amino acid sequence of SEQ ID No: 12.

8. The fusion protein according to claim 6, wherein the peptide derived from protein A is BC domain having an amino acid sequence of SEQ ID No: 13.

9. The fusion protein according to claim 1, wherein the protein A or the peptide derived from protein A is fused to the N-terminus or C-terminus of the mussel adhesive protein or the peptide derived from a mussel adhesive protein.

10. The fusion protein according to claim 1, which has an amino acid sequence of SEQ ID No: 14.

11. A polynucleotide encoding the fusion protein of claim 1.

12. The polynucleotide according to claim 11, which has a nucleotide acid sequence of SEQ ID No: 15.

13. A recombinant vector comprising the polynucleotide of claim 12.

14. A transformed cell comprising the recombinant vector of claim 13.

15. A method of preparing the fusion protein of claim 1 by culturing the transformed cell of claim 14.

16. A biochip comprising a solid substrate to which the fusion protein of claim 1 is attached.

17. The biochip according to claim 16, wherein the solid substrate is one or more selected group consisting of glass, modified or functionalized glass, plastics, polysaccharides, nylon or nitrocellulose, resins, silica or silica-based materials including silicon and modified silicon, carbon, metals, and inorganic glasses, and wherein the plastics include acrylic, polystyrene, copolymers of styrene and other materials, polypropylene, polyethylene, polybutylene, polyurethanes, Teflon and tetrafluoroethylene.

18. A method for detecting antigen, which comprises the steps of:
    immobilizing an antibody which specifically binds to the target antigen on the solid substrate of the biochip of claim 16;
    adding a biological sample comprising the target antigen to the biochip; and
    detecting the target antigen by measuring antigen-antibody interactions.

19. The method according to claim 18, wherein the biological sample is one or more selected from the group consisting of plasma, blood, saliva, interstitial fluid, serum, urine, synovial, cerebrospinal, lymph, seminal, amniotic, pericardial fluid and ascites.

* * * * *

```
                         SEQUENCE LISTING

<160> NUMBER OF SEQ ID NOS: 15

<210> SEQ ID NO 1
<211> LENGTH: 41
<212> TYPE: DNA
<213> ORGANISM: Artificial Sequence
<220> FEATURE:
<223> OTHER INFORMATION: forward primer for MAP protein

<400> SEQUENCE: 1
gggcccatgg ggtggcggag ggagctctga agaatataaa g                          41

<210> SEQ ID NO 2
<211> LENGTH: 38
<212> TYPE: DNA
<213> ORGANISM: Artificial Sequence
<220> FEATURE:
<223> OTHER INFORMATION: reverse primer for MAP protein

<400> SEQUENCE: 2
cgcgctcgag gctgctgccg ccataatatt ttttatag                              38

<210> SEQ ID NO 3
<211> LENGTH: 35
<212> TYPE: DNA
<213> ORGANISM: Artificial Sequence
<220> FEATURE:
<223> OTHER INFORMATION: forward primer for BC protein

<400> SEQUENCE: 3
gcgccatatg gataacaaat tcaacaaaga acaac                                 35

<210> SEQ ID NO 4
<211> LENGTH: 35
<212> TYPE: DNA
<213> ORGANISM: Artificial Sequence
<220> FEATURE:
<223> OTHER INFORMATION: reverse primer for BC protein

<400> SEQUENCE: 4
gcgcccatgg ttttggtgct tgagcatcgt ttagc                                 35

<210> SEQ ID NO 5
<211> LENGTH: 35
<212> TYPE: DNA
<213> ORGANISM: Artificial Sequence
<220> FEATURE:
<223> OTHER INFORMATION: reverse primer for BC protein

<400> SEQUENCE: 5
gcgcctcgag ttttggtgct tgagcatcgt ttagc                                 35
```

```
<210> SEQ ID NO 6
<211> LENGTH: 75
<212> TYPE: PRT
<213> ORGANISM: Mytilus galloprovincialis

<400> SEQUENCE: 6

Ser Ser Glu Glu Tyr Lys Gly Gly Tyr Tyr Pro Gly Asn Thr Tyr His
  1               5                  10                  15

Tyr His Ser Gly Gly Ser Tyr His Gly Ser Gly Tyr His Gly Gly Tyr
             20                  25                  30

Lys Gly Lys Tyr Tyr Gly Lys Ala Lys Tyr Tyr Lys Tyr Lys
         35                  40                  45

Asn Ser Gly Lys Tyr Lys Tyr Leu Lys Lys Ala Arg Lys Tyr His Arg
     50                  55                  60

Lys Gly Tyr Lys Lys Tyr Tyr Gly Gly Ser Ser
 65                  70                  75

<210> SEQ ID NO 7
<211> LENGTH: 500
<212> TYPE: PRT
<213> ORGANISM: Staphylococcus aureus

<400> SEQUENCE: 7

Met Lys Lys Asn Ile Tyr Ser Ile Arg Lys Leu Gly Val Gly Ile
  1               5                  10                  15

Ala Ser Val Thr Leu Gly Thr Leu Leu Ile Ser Gly Gly Val Thr Pro
             20                  25                  30

Ala Ala Asn Ala Ala Gln His Asp Glu Ala Gln Gln Asn Ala Phe Tyr
             35                  40                  45

Gln Val Leu Asn Met Pro Asn Leu Asn Ala Asp Gln Arg Asn Gly Phe
     50                  55                  60

Ile Gln Ser Leu Lys Asp Asp Pro Ser Gln Ser Ala Asn Val Leu Gly
 65                  70                  75                  80

Glu Ala Gln Lys Leu Asn Asp Ser Gln Ala Pro Lys Ala Asp Ala Gln
             85                  90                  95

Gln Asn Asn Phe Asn Lys Asp Gln Gln Ser Ala Phe Tyr Glu Ile Leu
        100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255
```

```
Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
            275                 280                 285

Pro Asn Leu Thr Glu Gln Arg Asn Gly Phe Ile Gln Ser Leu Lys
            290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Asp Asn Asn Lys Pro Gly Lys
                325                 330                 335

Glu Asp Asn Asn Lys Pro Gly Lys Glu Asp Asn Lys Pro Gly Lys
            340                 345                 350

Glu Asp Gly Asn Lys Pro Gly Lys Glu Asp Asn Lys Lys Pro Gly Lys
            355                 360                 365

Glu Asp Asn Lys Lys Pro Gly Lys Glu Asp Asn Lys Lys Pro Gly Lys
            370                 375                 380

Glu Asp Gly Asn Lys Pro Gly Lys Glu Asp Asn Lys Lys Pro Gly Lys
385                 390                 395                 400

Glu Asp Gly Asn Gly Val His Val Val Lys Pro Gly Asp Thr Val Asn
                405                 410                 415

Asp Ile Ala Lys Ala Asn Gly Thr Thr Ala Asp Lys Ile Ala Ala Asp
            420                 425                 430

Asn Lys Leu Ala Asp Lys Asn Met Ile Lys Pro Gly Gln Glu Leu Val
            435                 440                 445

Val Asp Lys Lys Gln Pro Ala Asn His Ala Asp Ala Asn Lys Ala Gln
450                 455                 460

Ala Leu Pro Glu Thr Gly Glu Glu Asn Pro Phe Ile Gly Thr Thr Val
465                 470                 475                 480

Phe Gly Gly Leu Ser Leu Ala Leu Gly Ala Ala Leu Leu Ala Gly Arg
                485                 490                 495

Arg Arg Glu Leu
            500

<210> SEQ ID NO 8
<211> LENGTH: 58
<212> TYPE: PRT
<213> ORGANISM: Staphylococcus aureus

<400> SEQUENCE: 8

Ala Asp Asn Asn Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 9
<211> LENGTH: 58
<212> TYPE: PRT
<213> ORGANISM: Staphylococcus aureus

<400> SEQUENCE: 9

Ala Asp Asn Lys Phe Asn Lys Glu Gln Gln Asn Ala Phe Tyr Glu Ile
1               5                   10                  15
```

```
Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Staphylococcus aureus

<400> SEQUENCE: 10

Ala Asp Asn Lys Phe Asn Lys Glu Gln Gln Asn Ala Phe Tyr Glu Ile
 1               5                  10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 11
<211> LENGTH: 59
<212> TYPE: PRT
<213> ORGANISM: Staphylococcus aureus

<400> SEQUENCE: 11

Ala Asp Asn Asn Phe Asn Lys Asp Gln Gln Ser Ala Phe Tyr Glu Ile
 1               5                  10                  15

Ile Asn Met Pro Asn Leu Asn Glu Ala Gln Asn Arg Asn Gly Phe Ile
            20                  25                  30

Gln Ser Leu Lys Ile Asp Pro Ser Gln Ser Thr Asn Val Leu Gly Glu
        35                  40                  45

Ala Lys Lys Leu Asn Glu Ser Gln Ala Pro Lys
    50                  55

<210> SEQ ID NO 12
<211> LENGTH: 59
<212> TYPE: PRT
<213> ORGANISM: Staphylococcus aureus

<400> SEQUENCE: 12

Ala Asp Ala Gln His Asp Glu Ala Gln Gln Asn Ala Phe Tyr Glu Ile
 1               5                  10                  15

Ile Asn Met Pro Asn Leu Asn Glu Glu Gln Asn Arg Asn Gly Phe Ile
            20                  25                  30

Gln Ser Leu Lys Ile Asp Pro Ser Gln Ser Ala Asn Leu Leu Ser Glu
        35                  40                  45

Ala Lys Lys Leu Asn Glu Ser Gln Ala Pro Lys
    50                  55

<210> SEQ ID NO 13
<211> LENGTH: 116
<212> TYPE: PRT
<213> ORGANISM: Staphylococcus aureus

<400> SEQUENCE: 13

Ala Asp Asn Lys Phe Asn Lys Glu Gln Gln Asn Ala Phe Tyr Glu Ile
```

```
            1               5                   10                  15
Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
                35                  40                  45

Lys Lys Leu Asn Asp Ala Gln Ala Pro Lys Ala Asp Asn Lys Phe Asn
                50                  55                  60

Lys Glu Gln Gln Asn Ala Phe Tyr Glu Ile Leu His Leu Pro Asn Leu
 65                 70                  75                  80

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
                100                 105                 110

Gln Ala Pro Lys
        115
```

<210> SEQ ID NO 14
<211> LENGTH: 206
<212> TYPE: PRT
<213> ORGANISM: Artificial Sequence
<220> FEATURE:
<223> OTHER INFORMATION: Fusion protein

<400> SEQUENCE: 14

```
Met Ala Asp Asn Lys Phe Asn Lys Glu Gln Gln Asn Ala Phe Tyr Glu
 1               5                   10                  15

Ile Leu His Leu Pro Asn Leu Asn Glu Glu Gln Arg Asn Gly Phe Ile
                20                  25                  30

Gln Ser Leu Lys Asp Asp Pro Ser Gln Ser Ala Asn Leu Leu Ala Glu
                35                  40                  45

Ala Lys Lys Leu Asn Asp Ala Gln Ala Pro Lys Ala Asp Asn Lys Phe
                50                  55                  60

Asn Lys Glu Gln Gln Asn Ala Phe Tyr Glu Ile Leu His Leu Pro Asn
 65                 70                  75                  80

Leu Thr Glu Glu Gln Arg Asn Gly Phe Ile Gln Ser Leu Lys Asp Asp
                85                  90                  95

Pro Ser Val Ser Lys Glu Ile Leu Ala Glu Ala Lys Lys Leu Asn Asp
                100                 105                 110

Ala Gln Ala Pro Lys Pro Trp Gly Gly Gly Ser Glu Glu Tyr
                115                 120                 125

Lys Gly Gly Tyr Tyr Pro Gly Asn Thr Tyr His Tyr His Ser Gly Gly
        130                 135                 140

Ser Tyr His Gly Ser Gly Tyr His Gly Gly Tyr Lys Gly Lys Tyr Tyr
145                 150                 155                 160

Gly Lys Ala Lys Lys Tyr Tyr Tyr Lys Tyr Lys Asn Ser Gly Lys Tyr
                165                 170                 175

Lys Tyr Leu Lys Lys Ala Arg Lys Tyr His Arg Lys Gly Tyr Lys Lys
                180                 185                 190

Tyr Tyr Gly Gly Ser Ser Leu Glu His His His His His His
                195                 200                 205
```

<210> SEQ ID NO 15
<211> LENGTH: 618
<212> TYPE: DNA
<213> ORGANISM: Artificial Sequence
<220> FEATURE:
<223> OTHER INFORMATION: polynucleotide encoding fusion protein

```
<400> SEQUENCE: 15
atggcggata acaaattcaa caaagaacaa caaaatgctt tctatgaaat cttacattta        60
cctaacttaa acgaagaaca acgcaatggt ttcatccaaa gcttaaaaga tgacccaagc       120
caaagcgcta accttttagc agaagctaaa aagctaaatg atgcacaagc accaaaagct       180
gacaacaaat tcaacaaaga acaacaaaat gctttctatg aaattttaca tttacctaac       240
ttaactgaag aacaacgtaa cggcttcatc caaagcctta aagacgatcc ttcagtgagc       300
aaagaaattt tagcagaagc taaaaagcta aacgatgctc aagcaccaaa accatggggt       360
ggcggaggga gctctgaaga atataaaggc ggctattatc cgggcaacac ctaccattat       420
cattctggcg gcagctatca tggctctggc tatcatggcg gctataaagg caaatattat       480
ggcaaagcga aaaaatatta ttataaatat aaaaacagcg gcaaatataa atatctgaaa       540
aaagcgagaa aatatcatag aaaaggctat aaaaaatatt atggcggcag cagcctcgag       600
caccaccacc accaccac                                                     618
```